Figure 1:
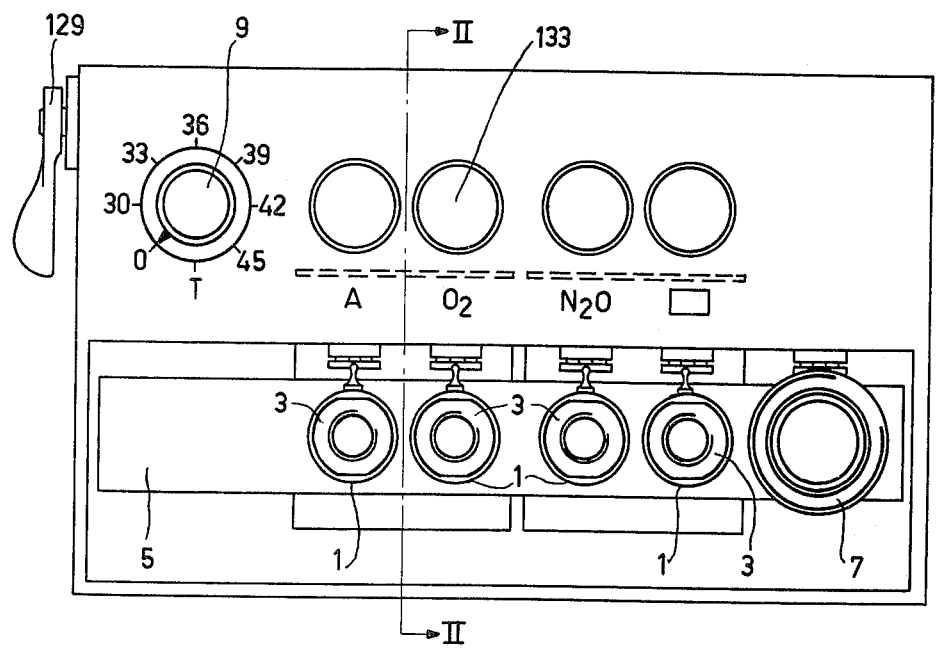

United States Patent [19]

Albarda

[11] 4,204,536
[45] May 27, 1980

[54] RESPIRATOR

[75] Inventor: Scato Albarda, Eindhoven, Netherlands

[73] Assignee: U.S. Philips Corporation, New York, N.Y.

[21] Appl. No.: 911,212

[22] Filed: Jun. 1, 1978

[30] Foreign Application Priority Data

Jun. 30, 1977 [NL] Netherlands .......................... 7707259

[51] Int. Cl.² .............................................. B61D 27/00
[52] U.S. Cl. ........................ 128/204.22; 128/203.25; 128/205.11; 128/205.24
[58] Field of Search ............... 128/210, 209, 211, 207, 128/208

[56] References Cited

U.S. PATENT DOCUMENTS

| 3,044,465 | 7/1962 | Anderson et al. | 128/210 |
| 4,022,202 | 5/1977 | Price | 128/210 |

Primary Examiner—Henry K. Artis
Attorney, Agent, or Firm—Thomas A. Briody; Jack Oisher; Jack E. Haken

[57] ABSTRACT

A respirator, comprising a number of controllers which are connected to a common duct and which serve to conduct different gases. Each controller comprises a gas passage provided with a displaceable closing member; a control member controls the position of the closing member, so that a predetermined gas flow occurs through the controller. To this end, the position of the closing member and the differential pressure across the passage are measured.

3 Claims, 7 Drawing Figures

RESPIRATOR

The invention relates to a respirator for administering a gas mixture of predetermined composition to a patient at a predetermined flow rate, comprising at least one controller for controlling a gas flow which is controlled by an electronic control member and which comprises a gas passage provided with a displaceable closing member.

A respirator of this kind is known from Netherlands Patent Application 73 04 255 laid open to public inspection. This apparatus is comparatively complex and hence expensive and susceptible to breakdowns, while the changing of the composition and the rate of flow of the gas administered to the patient is not simple. The invention has for its object to provide a respirator which is substantially simpler and in which the amount of gas as well as the gas composition can be controlled by electrical signals. The controller can be readily sterilized.

To this end, the respirator in accordance with the invention is characterized in that the controller is formed by a valve, the closing member consisting of a ball which closes the gas passage in one position and which can be displaced, by means of a pin which is displaceable in its longitudinal direction by way of a drive system, so that it gradually further releases the gas passage, a defined relationship existing between the gas flow through the valve and the differential gas pressure between both sides of the gas passage, and also the position of the ball. A position sensor for indicating the position of the ball and a pressure sensor for determining said differential pressure are also provided. The control member is adapted to displace the ball, using the drive system, on the basis of the differential pressure, the position of the ball, and an adjusted desired gas flow, so that the desired gas flow passes through the valve in accordance with said relationship between these quantities.

The invention will be described in detail hereinafter with reference to the accompanying diagrammatic drawing.

Figure 2:
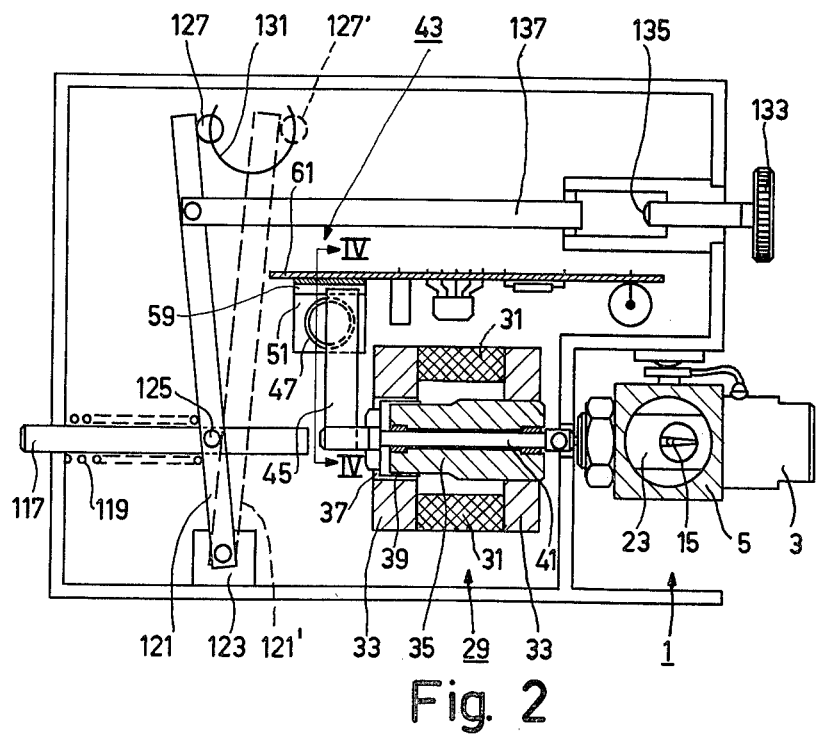
Figure 3:
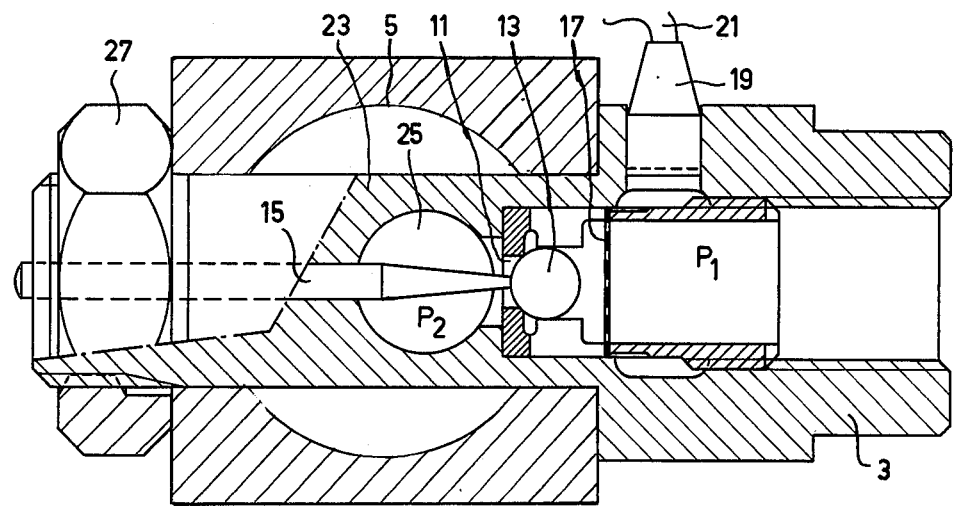
Figure 4:
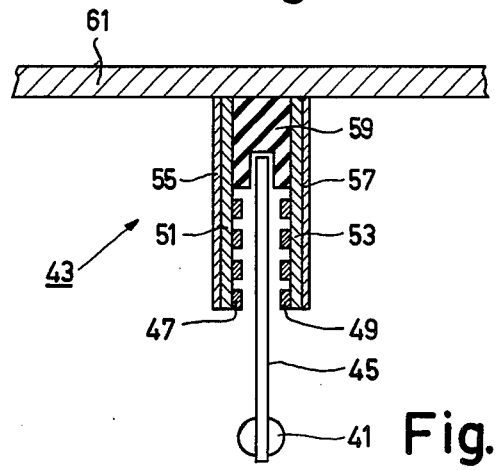
Figure 5:
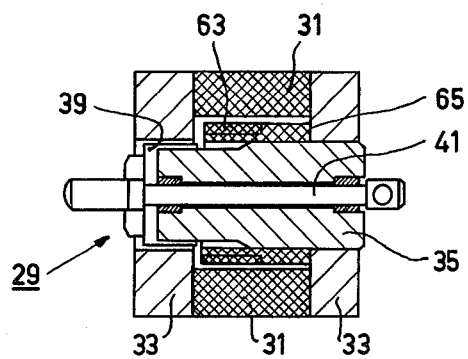
Figure 6:
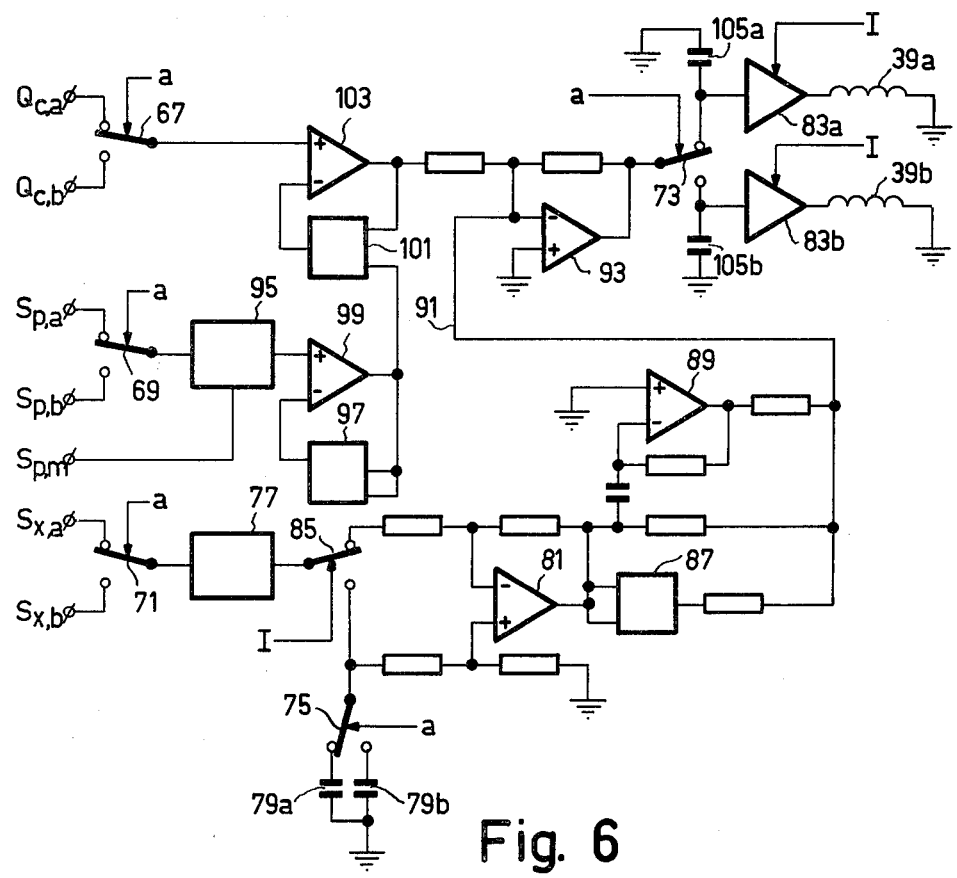
Figure 7:
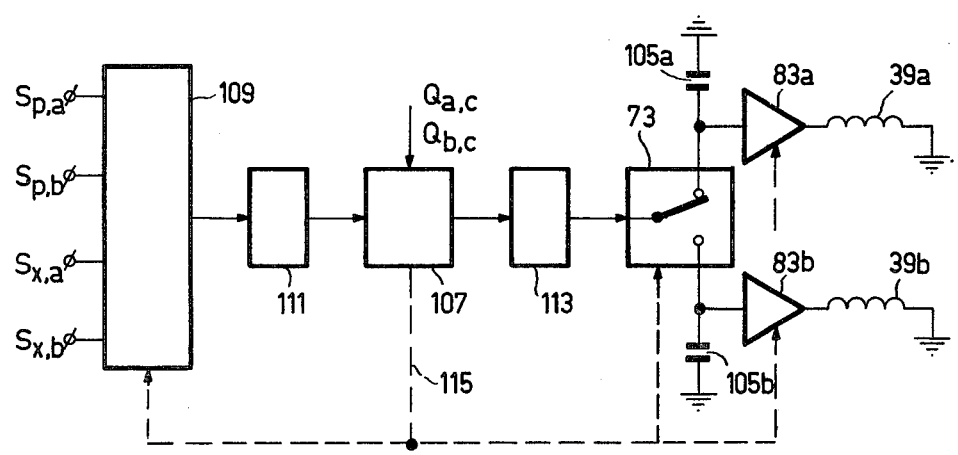

FIG. 1 is a front view of an embodiment of a respirator in accordance with the invention, FIG. 2 is a cross-sectional view of the respirator shown in FIG. 1, FIG. 3 is a longitudinal sectional view at an increased scale of a controller for the respirator shown in the FIGS. 1 and 2, FIG. 4 shows a detail of the respirator shown in the FIGS. 1 and 2, FIG. 5 shows a part of a further embodiment of the respirator in accordance with the invention, FIG. 6 shows a block diagram of a first embodiment of a control member for a respirator in accordance with the invention, and FIG. 7 shows a block diagram of a second embodiment of such a control member.

The respirator shown in the FIGS. 1 and 2 comprises four controllers 1, each of which comprises a connection 3 for connecting the controller to a gas duct (not shown). The gas flowing through the controller 1 arrives in a common duct 5 which may be connected to a patient by way of a patient connection 7.

The four gas ducts contain, from left to right in FIG. 1, for example, air (denoted by "A"), oxygen ($O_2$), laughing gas ($N_2O$) and a fourth gas yet to be selected. Furthermore water vapour can be added to the gas mixture by means of a known humidifier, for example, a vaporizer whose temperature can be adjusted by means of a knob 9.

As is shown in FIG. 3, the controller 1 is formed by a ball valve comprising a gas passage 11 which can be closed by means of a closing member in the form of a ball 13. In the position shown, the ball 13 is pressed against the gas passage 11 by the differential pressure between the pressure $P_1$ in the gas duct and the pressure $P_2$ in the common duct 5, the ball thus closing this passage. The ball 13 can be pushed out of the gas passage 11 (to the right in FIG. 3) by means of a pin 15 which is displaceable in its longitudinal direction. The further the ball is displaced to the right, the lower the resistance experienced by the gas flowing through the passage. The gas flow through the gas passage 11 can thus be accurately influenced. The movement of the ball 13 is limited by a perforated plate 17 which also prevents the ball from dropping out of the controller when the latter is not connected to a pressurized gas duct.

The pressure $P_1$ in the gas duct is liable to vary substantially. This pressure is measured by means of a known pressure sensor 19, which may comprise, for example, a diaphragm with strain gauges and which is connected to a measuring apparatus via a cable 21.

The pin 15 is journalled to be axially displaceable in a valve housing 23 in which an opening 25 is recessed to form the connection between the gas passage 11 and the common duct 5. The valve housing 23 is connected to the common duct 5 by way of a nut 27. The left end of the pin 15 projects from the valve housing 23 and cooperates with a drive system 29 (see FIG. 2). This system consists of two magnets 31 which generate, via yokes 33 and a core 35, a magnetic field in an air gap 37 which accommodates a drive coil 39 which is connected to a drive rod 41 which is journalled to be axially movable in an aperture in the core, the right end of said drive rod contacting the left end of the pin 15. A drive system of this kind has already being proposed in allowed U.S. patent application Ser. No. 802,905 now U.S. Pat. No. 4,106,029. When a direct current of suitable direction flows through the drive coil 39, the drive coil, and also the drive rod 41, moves to the right, so that the pin 15 forces the ball 13 out of the gas passage 11. An equilibrium then arises between the force directed to the left and exerted on the ball 13 by the gas flow and the force directed to the right and exerted by the energized drive coil 39, with the result that the ball comes to rest in a given position.

The position of the ball can be determined by means of a position sensor 43, a longitudinal sectional view of which is shown in FIG. 2, while FIG. 4 shows a cross-sectional view thereof. The sensor comprises a metal vane 45 which is connected to the free end of the drive rod 41 and which slides into the space between two coils 47 and 49 in dependence of the position of the drive rod, so that the coupling between these coils depends on the position of the drive rod and hence also on the position of the ball 13. The coils 47 and 49 are constructed as printed wiring provided on one side of insulating plates 51 and 53, respectively, the other side of which is provided with an earthed metal cover 55 and 57, respectively, which serves as a shield. The two plates 51, 53 are connected to each other with a spacer 59 and to a printed wiring board 61. The spacer 59 also serves to guide the free end of the vane 45. The coil 47 is connected to a transmitter (not shown) which is mounted on the board 61 and the coil 49 is connected to a receiver (not shown) which is also mounted on the board 61. For a given strength of the signal generated by the transmitter, the strength of the signal received is a measure for the position of the ball 13. The circuits of the transmitter and the receiver are known per se and need not be elaborated herein.

FIG. 5 is a longitudinal sectional view of a further embodiment of the position sensor. The position sensor is formed by a measuring coil 63 which is included in the drive system 29. This coil is wound on a coil former 65 which is mounted on the core 35. A measuring voltage having a frequency of, for example, 500 kHz is applied to the drive coil 39, together with the drive voltage for displacing the ball 13. The strength of the 500 kHz signal received by the measuring coil 63 is then a measure for the distance between the two coils, and hence for the position of the ball 13.

In both embodiments described, the position of the ball 13 is determined by measurement of the position of the drive rod 41. This is possible because the ball is constantly pressed against the right end of the pin 15 by the differential pressure $P_1 - P_2$, the right end of said pin in turn being pressed against the drive rod 41. This method of sensing the position of the ball 13 necessitates determination of the position of the drive rod in which the ball just closes the gas passage 11. This zero position may sometimes change, for example, when the ball valve is removed to be sterilized and is subsequently refitted, or when a new ball valve is mounted. There are various methods of determining this zero position, for example:

1. A given minimum force is required for displacement of the ball. Therefore, the current through the drive coil 39 can be chosen to be so small that the drive rod 41 moves to the right until it abuts against the pin 15. This is the zero position.

2. When the ball is displaced over only a very short distance (approximately 0.3 μm), immediately a clear hissing sound becomes audible; this sound can be readily detected by the pressure sensor 19 (which may act as a microphone). The occurrence of this sound determines the zero position of the drive rod 41.

The gas flow through a controller comprising a gas passage which can be closed by a closing member satisfies the general formula:

$$Q = K \cdot f(x) \cdot g(p) \quad (1)$$

Therein, Q is the gas flow, x is the distance over which the closing member is displaced with respect to its zero position, and p is the differential pressure between the two sides of the gas passage. The functions f and g can be experimentally or theoretically determined. For a ball as shown in FIG. 3, the following is applicable:

$$Q = \{Ax + Bx^2\}\sqrt{p} \quad (2)$$

For a ball valve comprising a ball having a diameter of 5 mm, the constants of this formula were found to have the following values:
A = 201.5,
B = −53.28.

q is then the gas flow in liters/minute when x is measured in mm and p is measured in atmospheres. For a gas flow of 156 l/min, a ball displacement of 0.8 mm is required at a differential pressure of 1.5 atmospheres, and a ball displacement of 0.39 mm is required at a differential pressure of 5 atmospheres.

It will be clear that a suitable control member which receives information as regards the differential pressure $p = P_1 - P_2$, the position x of the ball, and an adjusted desired gas flow $Q_c$, can control the current through the drive coil 29 on the basis of the formula (2) so that the ball 13 assumes exactly the correct position for obtaining a desired gas flow $Q_c$. A control member of this kind is preferably formed by an electronic circuit arranged on the board 61. FIG. 6 shows a block diagram of a first embodiment of such a circuit, which in this case controls two valves with drive coils 39a and 39b, respectively.

The circuit comprises five switches 67, 69, 71, 73 and 75, for example, relays or semiconductor switches which, in the state of the circuit shown in FIG. 6, are set to a position, by a control signal denoted by the reference a, in which the drive coil 39a is controlled. If the signal a is replaced by a signal b, these switches assume a position in which the drive coil 39b is controlled. Via the switch 71, a signal Sx, a or Sx, b, originating from the position sensor, is applied to a detector 77 which rectifies the signal, so that a voltage is formed which represents the value $x + x_0$, $x_0$ being the position of the ball in which the gas passage is closed. This value $x_0$ is stored in storage capacitors 79a, 79b, respectively, and is subtracted from the output voltage of the detector 77 in an amplifier 81 in order to obtain the value $-Ax$. The value $x_0$ is measured in accordance with the described method 1 by sending a small current through the drive coils 39 during the expiration phase so that the drive rod 41 is in the zero position. To this end, the output amplifiers 83a and 83b, supplying the current for the drive coils 39a and 39b, respectively, are adapted so that they are actuated by a signal I which is present during the inspiration phase. During the expiration phase, the signal I is not present and the amplifiers 83 supply a constant, small current which keeps the drive rods 41 exactly in the zero position. The signal then supplied by the position sensors produces the voltage $x_0$ on the output of the detector 77, said voltage being applied to the storage capacitors 79 via a switch 85. The switch 85 may be of the same type as the other switches and is operated, like the amplifiers 83, by the signal I. When this signal I is present the switch 85 assumes the position shown and when the signal I is absent, this switch connects the output of the detector to one of the storage capacitors 79.

On the basis of the voltage $-Ax$, a multiplier 87 forms a voltage $-Bx^2$ which is applied, together with the voltage $-Ax$ and a voltage $-Cx$ formed in an amplifier 89 (an attenuation term for the elimination of undesired dynamic effects), to a control amplifier 93 via a lead 91.

Via the switch 69, the signal Sp, a or Sp, b (proportional to the pressure $P_1$), originating from the pressure sensor 19, is applied to a pressure gauge 95 which also receives a signal Sp,m, proportional to the pressure $P_2$, and which forms a voltage p therefrom which is proportional to the differential pressure $P_1 - P_2$. This voltage is converted, by means of a multiplier 97 and an amplifier 99, into a voltage $\sqrt{p}$ which is applied to a multiplier 101.

The switch 67 applies an adjustable voltage Qc, a or Qc, b (proportional to the desired gas flow) to an amplifier 103 which is connected to the multiplier 101 so that on its output a voltage $Q_c/\sqrt{p}$ appears which is applied, together with the voltage $-Ax^2-Bx-Cx$ present on the lead 91, to the control amplifier 93. It appears from the formula (2) that, when x has the correct value $x_c$, the following must be applicable:

$$(Qc/\sqrt{p})-Ax-Bx^2=0 \qquad (3)$$

In that case, x no longer changes, so that x=0.

As long as the equation (3) is not satisfied, $x \neq x_c$ and the control amplifier 93 produces an output signal which is applied, via the switch 73, as a correction signal to the input of one of the output amplifiers 83a and 83b, and also to a capacitor 105a or 105b, respectively, connected to this input, so that the last known correction signal is also applied to the amplifier 83a during the period in which the switch 73 is connected to the other amplifier 83b, and vice versa. The switches 67 ... 75 are controlled, for example, by means of a signal which has a frequency of 4 kHz, so that the signal a and the signal b are alternately present for a period of 125 μs.

FIG. 7 shows a block diagram of a second embodiment of a control member in which use is made of an integrated computing circuit (so-termed microprocessor) 107. The analog signals Sp,a, Sp,b, Sx,a, Sx,b are put in series by way of an analog sensor 109 and are subsequently applied in digital form, via an analog-to-digital converter 111, to the microprocessor 107. The signals Qa,c and Qb,c are directly applied in digital form to the microprocessor, for example, by means of a keyboard or by coding switches, (not shown). The microprocessor 107 calculates the correction signal on the basis of these data:

$$\Delta x=(Qc/\sqrt{p})-Ax-Bx^2-Cx.$$

This signal is applied, via a digital-to-analog converter 113 and the switch 73, to the amplifiers 83a, 83b. Via a test line 115 (denoted by a broken line), the microprocessor 107 controls the sensor 109, the switch 73 and the amplifiers 83.

The control member of the described embodiments is adapted to control two controllers, denoted by the references a and b. For the respirator shown in the FIGS. 1 and 2, comprising four controllers, therefore, two of such control members are necessary. Obviously, it is alternatively possible to construct the described control members so that they are capable of controlling four or more controllers.

If due to a fault the control member were no longer capable of operating the valve, these valves would automatically close due to the differential pressure $P_1-P_2$. In that case, gas would no longer be administered to the patient, which is of course undesirable. In order to ensure that gas is administered to the patient also in such a case, an auxiliary device is provided for mechanically keeping open at least one of the valves. This auxiliary device (see FIG. 2) comprises a push rod 117 which can be pressed against the left end of the drive rod 41 by a helical spring 119. Normally, this is prevented by a connecting rod 121 which is connected to the housing of the respirator by means of a hinge 123 and to the push rod 117 by means of a shaft 125. The free end of the connecting rod rests against a cam 127 which can be placed in one or two positions by means of a control knob 129 (see FIG. 1). When the control knob 129 is turned, the cam 127 moves along the arc of a circle 131 to the second position which is denoted by a broken line and the reference 127'. Under the influence of the spring 119, the connecting rod 121 also moves to the right until it reaches the second position denoted by a broken line and the reference 121'. The push rod 117 then presses against the left end of the drive rod 41 which thus opens the ball valve. The size of the passage, and hence the conducted gas flow, can be determined in advance by means of an adjusting knob 133 for shifting an abutment 135 which cooperates with a transverse rod 137, connected to the connecting rod 121, in order to limit the movement of the connecting rod to the right. By means of the adjusting knob 133, the second position 121' of the connecting rod can thus be controlled independent of the second position 127' of the cam. In an emergency, it is merely necessary to switch over the control knob 129 in order to activate the gas flow to the patient adjusted in advance by means of the adjusting knob 133. Obviously, the auxiliary device can also be automatically actuated, for example, in the case of a power failure.

What is claimed is:

1. A respirator for administering a gas mixture of predetermined composition to a patient at a predetermined flow rate, comprising at least one controller for controlling a gas flow which is controlled by an electric control member and which comprises a gas passage provided with a displaceable closing member, wherein:

the controller (1) comprises a valve having a closing member including a ball (13) which closes the gas passage (11) in one position and which is displaceable, by a pin (15) which is displaceable in a longitudinal direction by a drive system (29), to gradually open the gas passage (11), a defined relationship existing between gas flow through the valve (1), differential gas pressure across both sides of the gas passage (11), and the position of the ball (13); and further comprising position sensor means (43) which indicate the position of the ball (13); and pressure sensor means which measure (19) said differential pressure;

the control member functioning to displace the ball (13), using the drive system (29), on the basis of the differential pressure, the position of the ball (13) and an adjusted desired gas flow, so that the desired gas flow passes through the valve (1) in accordance with said relationship between these quantities.

2. A respirator as claimed in claim 1, wherein:

the position sensor (43) is connected to the drive system (29); and the control member comprises a storage element (79) which is connected to store a signal supplied by the position sensor (43) when the ball (13) just closes the gas passage (11).

3. A respirator as claimed in any of the preceding claims, comprising more than one controller (1), the input of each controller (1) being connected to a separate gas duct, the outputs of all controllers (1) being connected to a common duct (5).

* * * * *